(12) United States Patent
Mondro et al.

(10) Patent No.: US 8,956,309 B2
(45) Date of Patent: Feb. 17, 2015

(54) SENSOR STRIP POSITIONING MECHANISM

(75) Inventors: Jason Mondro, Franklin Lakes, NJ (US); David Schiff, Highland Park, NJ (US); Scott W. Gisler, Washingtonville, NY (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 70 days.

(21) Appl. No.: 12/689,643

(22) Filed: Jan. 19, 2010

(65) Prior Publication Data

US 2011/0178433 A1    Jul. 21, 2011

(51) Int. Cl.
| | | |
|---|---|---|
| *A61B 5/157* | (2006.01) | |
| *A61B 5/155* | (2006.01) | |
| *A61B 5/151* | (2006.01) | |
| *A61B 5/15* | (2006.01) | |
| *G01N 33/487* | (2006.01) | |
| *G01N 35/00* | (2006.01) | |

(52) U.S. Cl.
 CPC ............ *A61B 5/15146* (2013.01); *A61B 5/1411* (2013.01); *G01N 33/48764* (2013.01); *G01N 35/00009* (2013.01); *G01N 2035/00108* (2013.01)
 USPC ........... 600/583; 600/584; 436/44; 242/538.1

(58) Field of Classification Search
 CPC ............. A61B 5/1411; A61B 5/15165; A61B 5/15169; A61B 2562/043; A61B 2562/16; G01N 35/00009; G01N 35/00089; G01N 35/00108
 USPC ....... 600/583, 584; 606/181; 436/44; 422/66; 242/538.1
 See application file for complete search history.

(56) References Cited

U.S. PATENT DOCUMENTS

| | | | |
|---|---|---|---|
| 5,407,554 A | 4/1995 | Saurer | 204/403 |
| 5,437,999 A | 8/1995 | Diebold et al. | 435/288 |
| 5,741,634 A | 4/1998 | Nozoe et al. | 435/4 |
| 6,143,164 A | 11/2000 | Heller et al. | 205/777.5 |
| 6,558,402 B1 | 5/2003 | Chelak et al. | 606/182 |
| 6,878,345 B1 * | 4/2005 | Astle | 422/66 |
| 6,881,578 B2 | 4/2005 | Otake | 436/44 |
| 6,893,545 B2 | 5/2005 | Gotoh et al. | 204/403.04 |
| 7,192,405 B2 | 3/2007 | DeNuzzio et al. | 600/583 |
| 7,378,270 B2 * | 5/2008 | Azarnia et al. | 422/82.05 |
| 7,498,132 B2 | 3/2009 | Yu et al. | 435/6 |
| 7,731,900 B2 * | 6/2010 | Haar et al. | 422/66 |

(Continued)

FOREIGN PATENT DOCUMENTS

| | | |
|---|---|---|
| EP | 1 967 139 A1 | 9/2008 |
| EP | 2 275 034 A1 | 1/2011 |

(Continued)

OTHER PUBLICATIONS

European Search Report in EP 11151268.7, dispatch date: Jun. 15, 2011 (English) (6 pages).

*Primary Examiner* — Lee S Cohen
*Assistant Examiner* — Emily Lloyd
(74) *Attorney, Agent, or Firm* — Alan W. Fiedler; Fitzpatrick, Cella, Harper & Scinto

(57) ABSTRACT

A blood sample test device has a continuous strip sensor which is advanced through the device so that multiple blood sample tests can be conducted on a single strip. The device is provided with a sprocket having an encoder which engages sprocket holes on the strip to precisely control the advancement of the strip through the device.

17 Claims, 4 Drawing Sheets

(56) References Cited

U.S. PATENT DOCUMENTS

2002/0041829 A1 4/2002 Kowallis
2007/0020143 A1* 1/2007 Seidenstricker et al. ....... 422/66

FOREIGN PATENT DOCUMENTS

| WO | 2006/059241 A2 | 6/2006 |
| WO | 2007/077212 A2 | 7/2007 |

* cited by examiner

SENSOR STRIP POSITIONING MECHANISM

BACKGROUND OF THE INVENTION

1. Field of the Invention

The invention is in the field of blood sample acquisition and testing. In particular, the invention is directed to a sensor strip positioning mechanism used in a device that performs both a lancing operation to acquire a blood sample and a measurement operation on the sample in one user-initiated step. The strip is provided with a plurality of test sites, wound on a supply wheel and fed through the device between the supply wheel and a take-up wheel, so that a single strip may be used to obtain a plurality of measurements. According to the invention, a mechanism is provided to control the advancement of the strip in precise increments for proper alignment of the test sites in the device.

2. Description of the Related Art

Self-monitoring of blood glucose generally requires the user to extract a volume of capillary blood and place it on a disposable element for analysis. Devices for lancing a subject at an extraction site to obtain a small quantity of blood for testing on a test strip are known in the prior art. For example, U.S. Pat. No. 6,558,402, which is incorporated by reference, discloses a lancer having mechanisms for piercing a subject's skin and obtaining a sample.

Test strip sensing elements using amperometric and other techniques for determining the concentration of blood glucose in a blood sample are known in the prior art. U.S. Pat. Nos. 6,143,164, and 5,437,999, incorporated by reference herein, each disclose examples of test strip construction for electrochemical measurement of blood glucose.

The integration of lancing and sensing would be a desirable advance in the self-monitoring of blood glucose. U.S. patent application Ser. No. 12/502,594, filed Jul. 14, 2009, which is incorporated by reference, describes such a "two-in-one" device, wherein a single test strip contains a plurality of test sites, which can be advanced automatically through a testing device. Application Ser. No. 12/502,585, also filed Jul. 14, 2009 and incorporated by reference, describes fluid transport features that may be included on a continuous strip to facilitate the movement of a blood sample from the collection site to the test site. U.S. patent application Ser. No. 12/689,654 filed Jan. 19, 2010, and incorporated by reference, discloses an electrode layout on a continuous test strip which makes electrical contact with contacts in a device, producing signals which are used to control the advancement of the sensor strip. In this context, it would be desirable to have a mechanism to permit automatic advancement of the strip through the device in precise increments, that would account for changes in the effective diameter of the supply wheel and take-up wheel as the sensor strip is wound from one to the other as the strip is indexed through different stop points in the lancing/sensing process.

SUMMARY OF THE INVENTION

In one aspect, the invention is a blood sample test device, comprising: a supply wheel; a take-up wheel; a sensor strip on the supply wheel and the take-up wheel; and a motor engaging the supply wheel or the take up wheel to advance the sensor strip through the device. The sensor strip has a plurality of test sites arranged in series in a travel direction on the strip, such that each test site includes a lancet hole, first electrodes for determining a blood sample volume, and test electrodes for determining a blood sample characteristic. A sprocket with an associated encoder is provided having teeth that engage with sprocket holes in the continuous sensor strip. A processor operatively connected to the first electrodes, the test electrodes, the encoder and the motor controls advancement of the strip through the device.

DETAILED DESCRIPTION OF THE PREFERRED EMBODIMENTS

Figure 1:
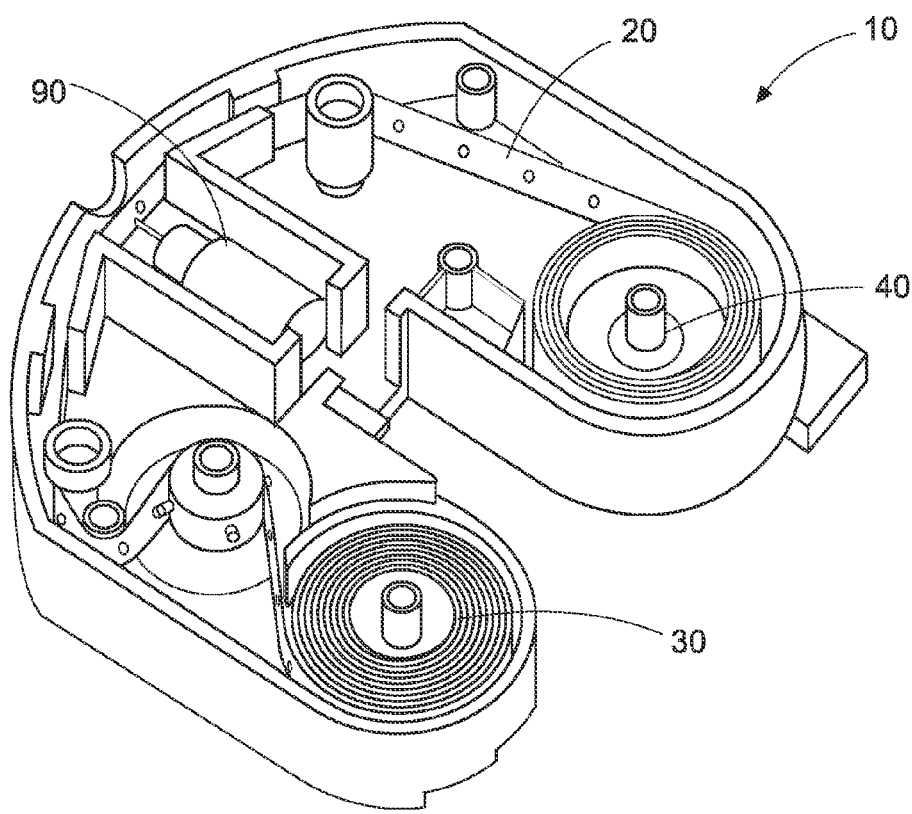
FIG. 1 depicts the strip path in a cartridge according to a preferred embodiment of the invention.

In the embodiment of FIG. 1, a cartridge 10 is provided having continuous sensor strip 20 which is wound on supply wheel 30 and take up wheel 40. As the sensor strip 20 advances, the effective diameter of the wheels changes. Thus, the identical amount of rotation imparted to the wheel by a motor would result in a greater or lesser linear distance on the sensor strip 20 being advanced through the device. However, optimal operation of the sensor requires accurate alignment of the test site in the opening 50 of the device, as well as alignment of device contacts (not shown) with electrodes on the sensor strip 20.

Figure 3:
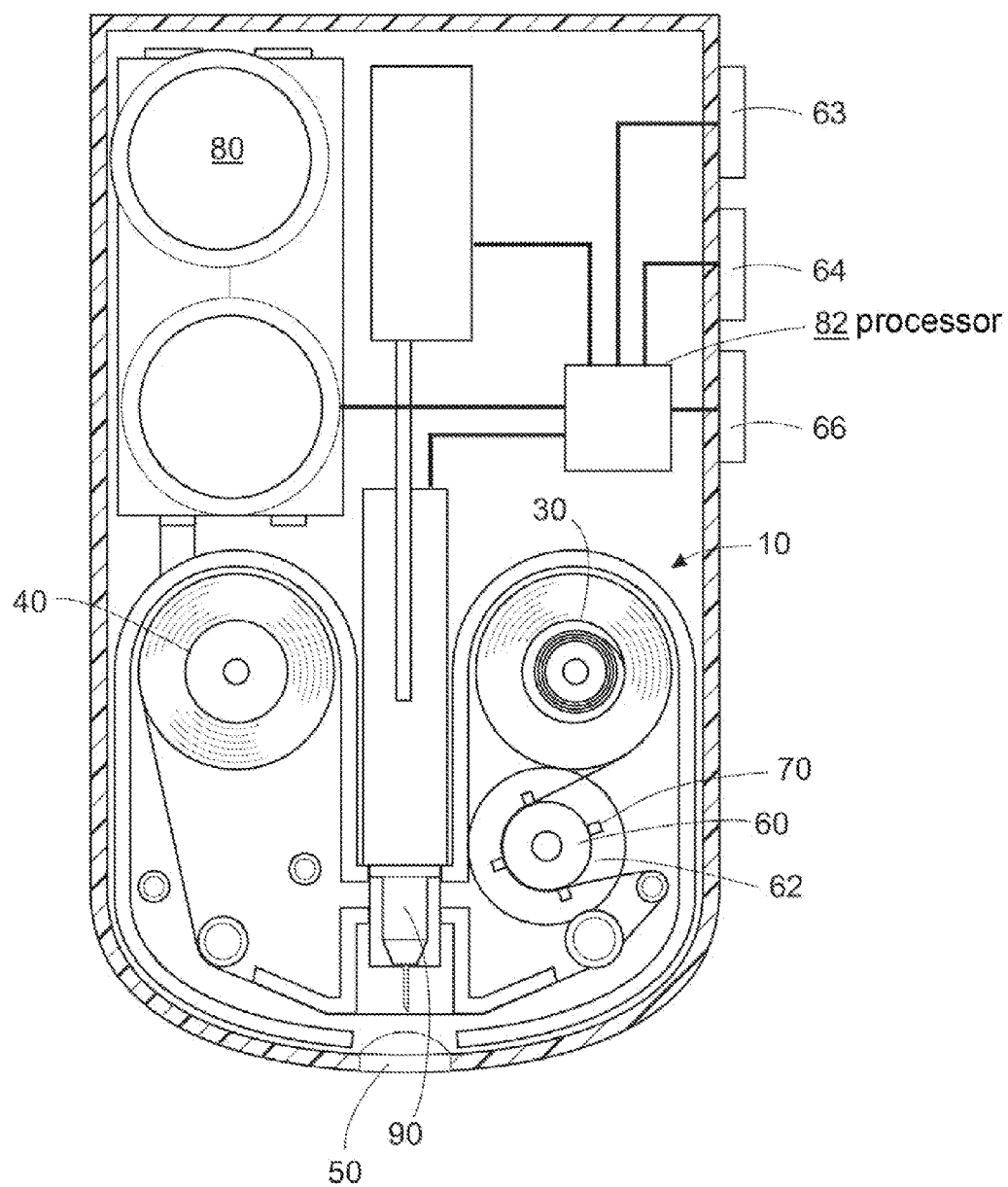
FIG. 3 depicts a sensor strip positioning mechanism in a unitary housing with a supply wheel, take up wheel, lancing mechanism, and power supply, user operated controls, display and processor for controlling different stages of the lancing and sensing operation.

As shown in FIG. 3, sprocket 60 is provided in the device with encoder 62 and sprocket teeth 70. The sprocket and/or encoder may be positioned in the device independently of the cartridge 10, so that the cartridge containing the sensor strip may be made detachable and removable by the user. The encoder registers the amount of linear distance that the strip advances and appropriate instructions are provided to the motor via processor 82. Because the distance the strip travels is obtained directly from features on the sensor strip, rather than rotation of the supply wheel or the take up wheel, accurate positioning is ensured.

Figure 4:
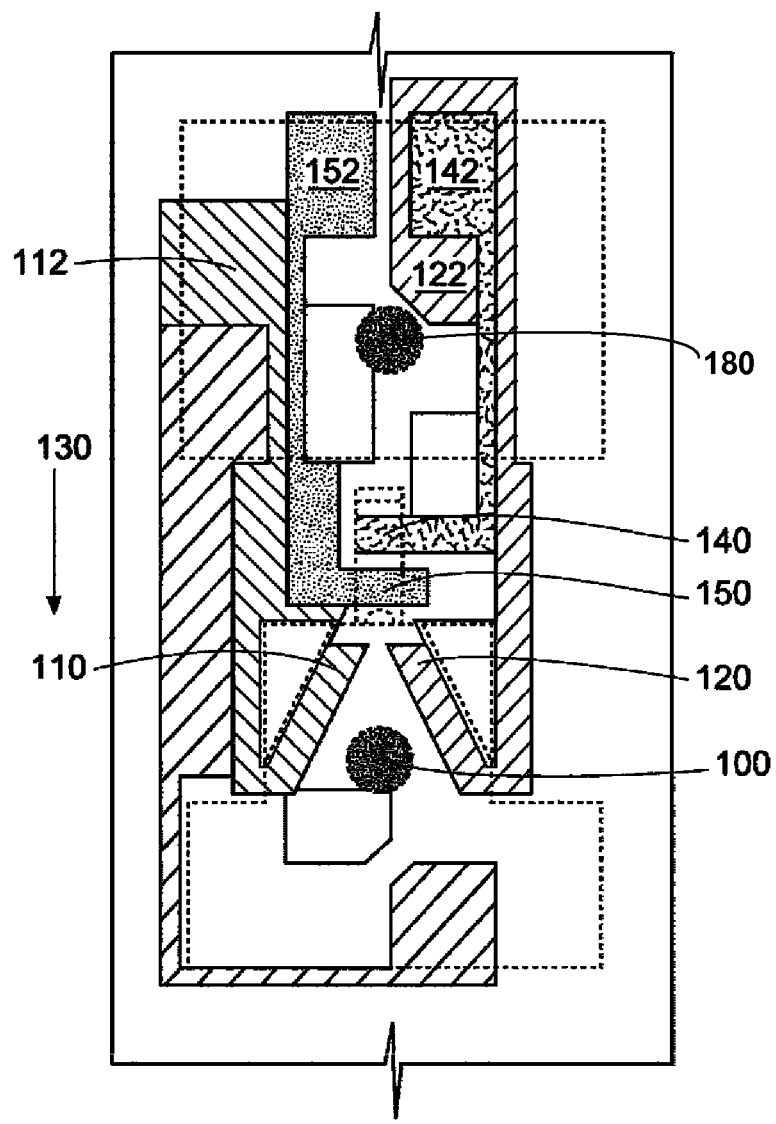
FIG. 4 depicts a test site on the continuous sensor strip 20.

As shown in FIG. 4, a test site on the strip comprises a lancet hole 100, through which lancet needle passes, and an area between electrodes 110 and 120 where a blood sample accumulates after a lancing operation. When the device is used, the cartridge can be positioned so that the cartridge opening 50 allows the user's skin to just touch the sensor strip. The lancet hole 100 on the strip lines up with lancet mechanism 90 and a lancing operation is performed. A blood sample accumulates on the sensor strip and when a sufficient volume is obtained, the electrodes 110 and 120 are shorted, signaling the sensor strip to advance in travel direction 130. As the strip advances, a portion of the blood sample travels along a capillary channel to a test site where a measurement, such as a blood glucose measurement, is conducted at a second pair of electrodes 140, 150. The user may interface with the device through user operable controls and display 63, 64, 66. In an alternative embodiment, gears (not shown) are provided that allow the strip to feed forward and backward, so that if an insufficient quantity of blood is obtained, the user can perform the lancing operation again using the same test site on the continuous strip.

Each test site on the sensor strip comprises a lancet hole, sensing electrodes which sense whether a sufficient volume has been detected, and a capillary channel between the sensing electrodes and the reagent wells where a blood characteristic is determined using a second set of electrodes. Each test site may be about 9 mm to about 19 mm in length, and the distance between the lancet holes of adjacent test sites on the strip may be in a range of about 20 mm to about 40 mm. The distance between sprocket holes 180 is in a range of about 10 mm and about 20 mm, and the diameter of the sprocket should be sized accordingly. An estimate of the sprocket diameter can be calculated by subtracting the strip thickness from the diameter that would be arrived at using simply the hole-to hole distance on the strip. The strip cannot be considered to have negligible thickness for the teeth to line up in the holes of the strip (see FIG. 2A).

Figure 2A:
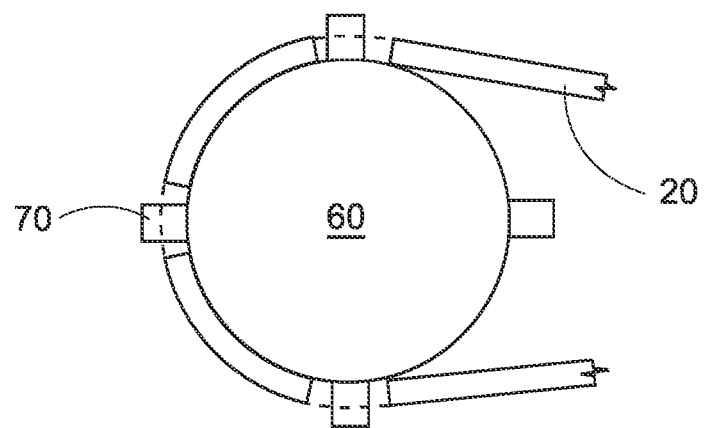
FIG. 2A depicts the engagement of sprocket teeth 70 with sprocket holes in the sensor strip 20 according to the invention.
Figure 2B:
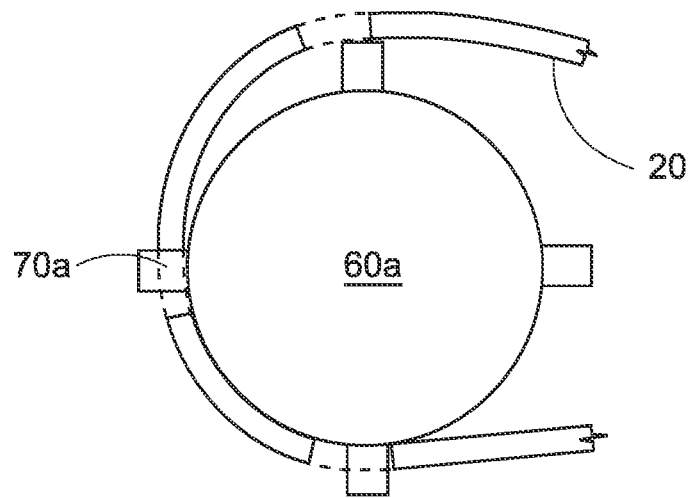
FIG. 2B depicts the engagement of sprocket teeth with sprocket holes in the sensor strip 20 according to a comparative example, including sprocket 60a and sprocket teeth 70a corresponding to the similarly numbered elements in the example of FIG. 2A according to the invention.

In FIG. 2A, the sprocket diameter is calculated taking into account the strip thickness (i.e., according to the invention) so that it is slightly smaller than a comparative example shown in FIG. 2B. In the comparative example of FIG. 2B, the sprocket diameter is too large, and the sensor strip slips off the sprocket teeth. In embodiments, the thickness of the sensor strip is in a range of about 10 mils to about 20 mils. The circumferential distance between individual teeth is thus about 9.5 mm to about 19.5 mm. The diameter of the sprocket is established based on the number of teeth, so that a sprocket having 4 teeth, for example, has a diameter in a range of about 12 mm to about 26 mm.

The sensor tape is made out of the materials conventionally used for this purpose and the method of construction would be known to those of ordinary skill in the art. For example, the substrate and structural layers of the strip defining wells and a capillary may be made from polyethylene terephthalate (PET), while the electrodes may be made from a layer of gold or other conductive material, deposited by sputtering or other known means, and patterned.

Processor 82 receives signals from the electrodes 110, 120, 140, and 150 via contact pads 112, 152, 122, and 142, which make contact with device contacts (not shown) in the device housing. The processor 82 also receives signals from the sprocket encoder, which encodes the distance traveled by the strip, and from user-operated controls. The processor coordinates these signals to provide instruction signals to the motor to advance the sensor strip, to the lancing mechanism to perform a lancing operation and to the test electrodes to perform a blood characteristic measurement. Processors which can be adapted for these purposes are commercially available and would be known to those of ordinary skill in the art. The elements are powered by any suitable power supply 80, such as a battery.

The foregoing description of the preferred embodiments is not to be deemed limiting of the invention, which is defined by the following claims.

What is claimed is:

1. A blood sample test device, comprising:
   a supply wheel;
   a take-up wheel;
   a motor configured to engage the supply wheel or the take-up wheel;
   a sensor strip on the supply wheel and the take-up wheel having a plurality of test sites arranged in series in a travel direction on the strip and a plurality of sprocket holes, wherein each test site of said plurality of test sites includes a first sprocket hole of said plurality of sprocket holes that also serves as a lancet hole, first electrodes for determining whether a sufficient volume of a blood sample is obtained, and test electrodes for determining a blood sample characteristic, and a second sprocket hole of said plurality of sprocket holes;
   a sprocket separate from the supply wheel and take-up wheel having an encoder configured to encode the distance traveled by the sensor strip and first and second sprocket hole teeth respectively configured to engage the first and second sprocket holes of each test site, wherein the diameter of the sprocket is configured to prevent the sensor strip from slipping off the first and second sprocket hole teeth by accounting for the thickness of the sensor strip; and
   a processor operatively connected to the first electrodes, the test electrodes, the encoder and the motor to control advancement of the sensor strip between the supply wheel and the take-up wheel.

2. The blood sample test device according to claim 1, further comprising a lancer mechanism, wherein the processor is operatively connected to the lancer mechanism to control a lancing operation to collect a blood sample on the sensor strip.

3. The blood sample test device according to claim 1, further comprising a display and user-operable controls.

4. The blood sample test device according to claim 1, wherein the motor is operatively engaged with the take-up wheel.

5. The blood sample test device according to claim 1, further comprising a removable cartridge comprising the sensor strip, supply wheel and take-up wheel.

6. The blood sample test device according to claim 1, wherein the diameter of the sprocket is between 12 mm and 26 mm.

7. A blood sample test device, comprising:
   (1) a removable cartridge, the cartridge comprising:
      (a) a supply wheel;
      (b) a take-up wheel; and
      (c) a sensor strip wound on the supply wheel and the take-up wheel having a plurality of test sites arranged in series in a travel direction on the strip and a plurality of sprocket holes, wherein each test site of said plurality of test sites includes a first sprocket hole of said plurality of sprocket holes that also serves as a lancet hole, first electrodes for determining whether a sufficient volume of a blood sample is obtained, and test electrodes for determining a blood sample characteristic, and a second sprocket hole of said plurality of sprocket holes;
   (2) a sprocket separate from the supply wheel and take-up wheel, the sprocket having first and second sprocket teeth respectively configured to engage the first and second sprocket holes of each test site, wherein the diameter of the sprocket is configured to prevent the sensor strip from slipping off the first and second sprocket hole teeth by accounting for the thickness of the sensor strip, and an encoder configured to encode the distance traveled by the sensor strip; and
   (3) a processor operatively connected to the first electrodes, the test electrodes, and the encoder to control advancement of the sensor strip between the supply wheel and the take-up wheel.

8. The blood sample test device according to claim 7, wherein the diameter of the sprocket is between 12 mm and 26 mm.

9. The blood sample test device according to claim 7, further comprising a display and user-operable controls.

10. A blood sample test device, comprising:
a supply wheel;
a take-up wheel;
a motor configured to engage the supply wheel or the take-up wheel;
a sensor strip on the supply wheel and the take-up wheel having a plurality of test sites arranged in series in a travel direction on the strip and a plurality of sprocket holes, wherein each test site of said plurality of test sites includes a first sprocket hole of said plurality of sprocket holes that also serves as a lancet hole, first electrodes for determining whether a sufficient volume of a blood sample is obtained, test electrodes for determining a blood sample characteristic, and a second sprocket hole of said plurality of sprocket holes;
a sprocket separate from the supply wheel and take-up wheel having an encoder configured to encode the distance traveled by the sensor strip and first and second sprocket teeth respectively configured to engage the first and second sprocket holes of each test site, wherein the distance between the first sprocket holes of two adjacent test sites is greater than the distance between the first and second sprocket holes of each of said test sites; and
a processor operatively connected to the first electrodes, the test electrodes, the encoder and the motor to control advancement of the sensor strip between the supply wheel and the take-up wheel.

11. The blood sample test device according to claim 10, wherein the distance between the first sprocket holes of said two adjacent test sites is between 20 mm and 40 mm, and the distance between the first and second sprocket holes of each of said test sites is between 10 mm and 20 mm.

12. The blood sample test device according to claim 10, further comprising a display and user-operable controls.

13. The blood sample test device according to claim 10, wherein the distance between the first sprocket holes of said two adjacent test sites is twice the distance between the first and second sprocket holes of each of said test sites.

14. A blood sample test device, comprising:
(1) a removable cartridge, the cartridge comprising:
 (a) a supply wheel;
 (b) a take-up wheel; and
 (c) a sensor strip wound on the supply wheel and the take-up wheel having a plurality of test sites arranged in series in a travel direction on the strip and a plurality of sprocket holes, wherein test site of said plurality of test sites includes a first sprocket hole of said plurality of sprocket holes that also serves as a lancet hole, first electrodes for determining whether a sufficient volume of a blood sample is obtained, test electrodes for determining a blood sample characteristic, and a second sprocket hole of said plurality of sprocket holes;
(2) a sprocket separate from the supply wheel and take-up wheel, the sprocket having first and second sprocket teeth respectively configured to engage the first and second sprocket holes of each test site, wherein the distance between the first sprocket holes of two adjacent test sites is greater than the distance between the first and second sprocket holes of each of said test sites, and an encoder configured to encode the distance traveled by the sensor strip; and
(3) a processor operatively connected to the first electrodes, the test electrodes, and the encoder to control advancement of the sensor strip between the supply wheel and the take-up wheel.

15. The blood sample test device according to claim 14, wherein the distance between the first sprocket holes of said two adjacent test sites is between 20 mm and 40 mm, and the distance between the first and second sprocket holes of each of said test sites is between 10 mm and 20 mm.

16. The blood sample test device according to claim 14, further comprising a display and user-operable controls.

17. The blood sample test device according to claim 14, wherein the distance between the first sprocket holes of said two adjacent test sites is twice the distance between the first and second sprocket holes of each of said test sites.

* * * * *